(12) United States Patent
Taylor

(10) Patent No.: US 8,022,360 B2
(45) Date of Patent: Sep. 20, 2011

(54) GAS PRE-CONCENTRATOR FOR DETECTION APPARATUS

(75) Inventor: Stephen John Taylor, Hyde Heath (GB)

(73) Assignee: Smiths Detection-Watford Limited (GB)

( * ) Notice: Subject to any disclaimer, the term of this patent is extended or adjusted under 35 U.S.C. 154(b) by 249 days.

(21) Appl. No.: 12/521,549

(22) PCT Filed: Dec. 10, 2007

(86) PCT No.: PCT/GB2007/004702
§ 371 (c)(1),
(2), (4) Date: Jun. 26, 2009

(87) PCT Pub. No.: WO2008/074981
PCT Pub. Date: Jun. 26, 2008

(65) Prior Publication Data
US 2010/0012834 A1    Jan. 21, 2010

(30) Foreign Application Priority Data
Dec. 20, 2006   (GB) .................................. 0625480.9

(51) Int. Cl.
*H01J 49/40* (2006.01)
*B01D 59/44* (2006.01)

(52) U.S. Cl. ........ 250/287; 250/288; 250/281; 250/282; 250/397; 250/428; 250/441.11; 422/176; 422/83

(58) Field of Classification Search ................... 250/287, 250/288, 281, 282, 397, 428, 441.11; 422/176, 422/83
See application file for complete search history.

(56) References Cited

U.S. PATENT DOCUMENTS

| | | |
|---|---|---|
| 3,107,966 A | 10/1963 | Bonhomme |
| 3,461,285 A | 8/1969 | Werner et al. |
| 3,470,527 A | 9/1969 | Bonhomme |
| 3,787,681 A | 1/1974 | Brunnee et al. |
| 4,378,499 A | 3/1983 | Spangler et al. |
| 4,551,624 A | 11/1985 | Spangler et al. |
| 5,083,019 A | 1/1992 | Spangler |
| 5,227,628 A | 7/1993 | Turner |
| 5,304,797 A | 4/1994 | Irie et al. |
| 5,574,277 A | 11/1996 | Taylor |
| 5,723,861 A | 3/1998 | Carnahan et al. |
| 5,854,431 A | 12/1998 | Linker et al. |
| 5,952,652 A | 9/1999 | Taylor et al. |
| 6,051,832 A | 4/2000 | Bradshaw |
| 6,073,498 A | 6/2000 | Taylor |
| 6,102,746 A | 8/2000 | Nania et al. |

(Continued)

FOREIGN PATENT DOCUMENTS

EP    0135747    4/1985

(Continued)

*Primary Examiner* — Nikita Wells
(74) *Attorney, Agent, or Firm* — Reinhart Boerner Van Deuren s.c.

(57) ABSTRACT

IMS apparatus has a preconcentrator in an inlet passage. A pressure pulser connected to the interior of a housing applies small alternating negative and positive pressure pulses to the housing so that air is drawn in and out of the inlet passage in a "panting" fashion. This causes analyte to be adsorbed by the preconcentrator but does not allow analyte to enter sufficiently to be ionized and detected. After a time sufficient to accumulate a detectable amount of analyte on the preconcentrator the apparatus switches to a desorb phase. The preconcentrator is heated to desorb the analyte, and the pressure pulser produces a larger negative pulse sufficient to draw the liberated analyte far enough into the reaction region for ionization and detection.

21 Claims, 1 Drawing Sheet

U.S. PATENT DOCUMENTS

| | | | |
|---|---|---|---|
| 6,225,623 B1 | 5/2001 | Turner et al. | |
| 6,239,428 B1 | 5/2001 | Kunz | |
| 6,442,997 B1 | 9/2002 | Megerle | |
| 6,459,079 B1 | 10/2002 | Machlinski et al. | |
| 6,481,263 B1 | 11/2002 | Haley | |
| 6,495,824 B1 | 12/2002 | Atkinson | |
| 6,502,470 B1 | 1/2003 | Taylor et al. | |
| 6,523,393 B1 | 2/2003 | Linker et al. | |
| 6,825,460 B2 | 11/2004 | Breach et al. | |
| 7,098,449 B1 | 8/2006 | Miller et al. | |
| 7,118,712 B1 | 10/2006 | Manginell | |
| 7,299,711 B1* | 11/2007 | Linker et al. | 73/863.23 |
| 7,311,566 B2 | 12/2007 | Dent | |
| 2002/0150923 A1 | 10/2002 | Malik | |
| 2004/0259265 A1 | 12/2004 | Ulrich | |
| 2005/0017163 A1 | 1/2005 | Miller et al. | |
| 2005/0095722 A1 | 5/2005 | McGill et al. | |
| 2005/0161596 A1 | 7/2005 | Guevremont et al. | |
| 2005/0178975 A1 | 8/2005 | Glukhoy | |
| 2005/0253061 A1 | 11/2005 | Cameron et al. | |
| 2006/0249673 A1 | 11/2006 | Breach et al. | |
| 2009/0090196 A1* | 4/2009 | Clark et al. | 73/863.12 |
| 2009/0090197 A1* | 4/2009 | Finlay et al. | 73/863.12 |
| 2010/0012833 A1* | 1/2010 | Taylor | 250/287 |
| 2010/0015722 A1* | 1/2010 | Taylor | 436/181 |
| 2010/0317125 A1* | 12/2010 | Taylor | 436/181 |

FOREIGN PATENT DOCUMENTS

| | | |
|---|---|---|
| GB | 2323165 | 9/1998 |
| WO | WO 9301485 | 1/1993 |
| WO | WO 9322033 | 11/1993 |
| WO | WO 9921212 | 4/1999 |
| WO | WO 0079261 | 12/2000 |
| WO | WO 0195999 | 12/2001 |
| WO | WO 02078047 | 10/2002 |
| WO | WO 2004012231 | 2/2004 |
| WO | WO 2006046077 | 5/2006 |
| WO | WO 2008035095 | 3/2008 |

* cited by examiner

GAS PRE-CONCENTRATOR FOR DETECTION APPARATUS

This application is related to three other concurrently filed copending patent applications, namely U.S. patent application Ser. No. 12/521,537, entitled "Detection Apparatus," U.S. patent application Ser. No. 12/521,542, entitled "Detection Apparatus," and U.S. patent application Ser. No. 12/521,546, entitled "Detector Apparatus and Preconcentrators," all assigned to the assignee of the present patent application, which three patent applications are hereby incorporated herein by reference.

BACKGROUND OF THE INVENTION

Field of the Invention

This invention relates to detector apparatus of the kind having an inlet and a preconcentrator located adjacent the inlet.

Ion mobility spectrometers or IMS apparatus are often used to detect substances such as explosives, drugs, blister and nerve agents, or the like. An IMS apparatus typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, UV source, or by corona discharge, and are admitted into the drift region of the cell by an electrostatic gate at one end. The ionized molecules drift to the opposite end of the cell at a speed dependent on the mobility of the ions. By measuring the time of flight along the cell, it is possible to identify the ions. In conventional IMS apparatus, clean dry gas flows continuously through the reaction or ionization region. This arrangement allows for continuous sampling and short recovery times. Where the sample analyte is only present in small concentrations in the sample gas, there may be a relatively low signal-to-noise ratio, and this can make reliable detection very difficult. It is known to use a preconcentrator at the inlet in order to produce a bolus of sample with increased levels of analyte. The preconcentrator contains an adsorbent material to which the analyte substance in gas supplied to the preconcentrator binds during an adsorption phase. The preconcentrator is subsequently heated to cause the analyte substance to be desorbed as a bolus of gas with increased concentration of analyte. Other forms of detectors also make use of preconcentrators. Preconcentrators can also be used to increase the concentration of a substance in other applications.

It is accordingly desirable to provide alternative detector apparatus and preconcentrators, and methods for the operation of the same.

SUMMARY OF THE INVENTION

According to one aspect of the present invention there is provided detector apparatus of the above-specified kind, characterized in that the detector apparatus is arranged and configured to cause an alternating flow of analyte gas or vapor across a preconcentrator during an adsorb phase such that there is a low or no net flow of gas or vapor into the detector apparatus and such that the analyte substance of interest is adsorbed by the preconcentrator, and that the detector apparatus is arranged and configured to cause the preconcentrator to desorb during a desorb phase and to interrupt the alternating flow and produce a net flow of gas or vapor into the detector apparatus such that the desorbed analyte substance is carried into the detector apparatus.

The detector apparatus may include a pressure pulser connected with the interior of the detector apparatus by which the alternating flow is caused. The detector apparatus may include a thermal device by which the preconcentrator is caused to desorb. The detector apparatus is preferably an IMS apparatus, with analyte gas or vapor being admitted during the desorb phase sufficiently to be ionized in a reaction region of the detector apparatus. The preconcentrator may be located in a passage opening into the interior of the detector apparatus.

According to another aspect of the present invention, there is provided a method of increasing the concentration of a substance, including the steps of: providing a pre-concentrator arranged to adsorb and desorb the substance; providing, during an adsorption phase, an alternating flow of gas or vapor within a passage and over the preconcentrator so that the substance is adsorbed by the preconcentrator and there is substantially no net flow of gas or vapor along the passage; and subsequently, during a desorption phase, causing the preconcentrator to desorb the adsorbed substance and provide a net flow of the gas or vapor along the passage so that the desorbed substance is carried with the gas or vapor along the passage.

According to a further aspect of the present invention, there is provided a preconcentrator apparatus that is arranged and configured to adsorb and desorb a substance, the preconcentrator apparatus including a gas flow path and an adsorbent material within the gas flow path, characterized in that the preconcentrator apparatus includes an arrangement for providing, during an adsorption phase, an alternating flow of gas or vapor over the preconcentrator and along in the gas flow path so that the substance is adsorbed by the preconcentrator and there is substantially no net flow of gas or vapor along the path, that the preconcentrator apparatus is arranged to cause the preconcentrator to desorb the adsorbed substance during a subsequent desorption phase, and that the preconcentrator apparatus is arranged and configured to provide a net flow of gas or vapor along the gas flow path during the desorption phase so that the desorbed substance is carried with the gas or vapor along the gas flow path.

The arrangement for providing the alternating gas flow may also include a pressure pulser.

DESCRIPTION OF THE DRAWINGS

An IMS apparatus that is constructed and operated according to the present invention will now be described, by way of example, with reference to the accompanying drawings, in which.

DETAILED DESCRIPTION OF THE PREFERRED EMBODIMENT

Figure 1:
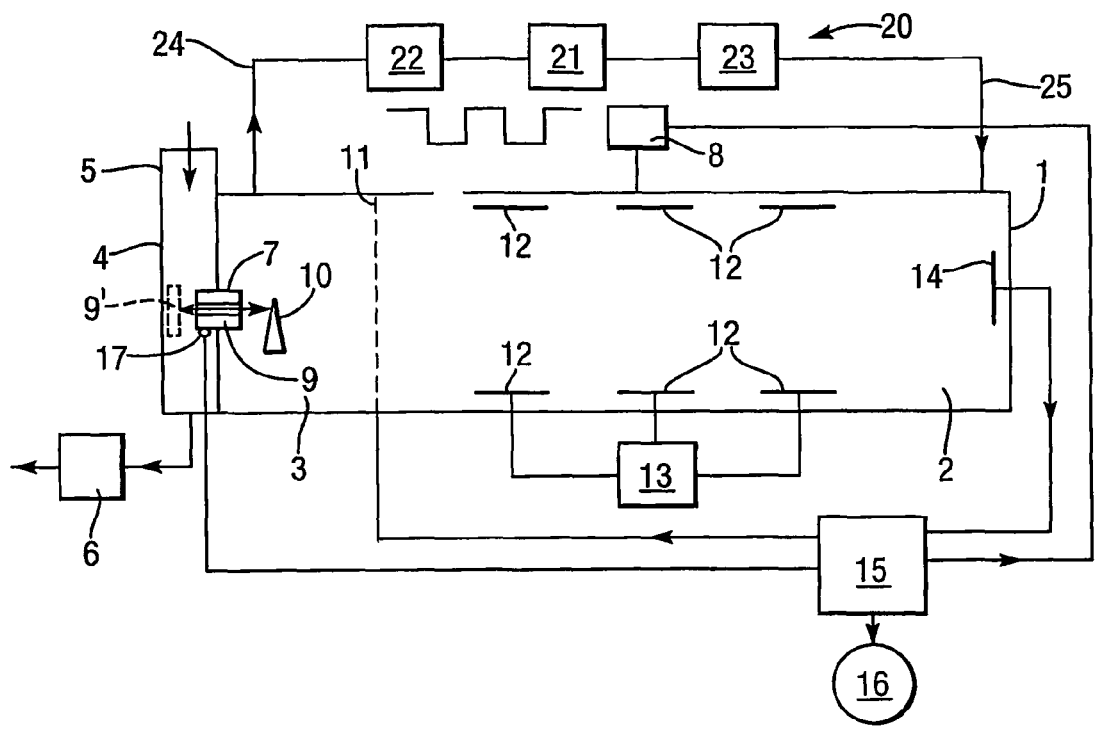
FIG. 1 shows the apparatus schematically during an adsorb phase.

With reference first to FIG. 1, the apparatus takes the form of an ion mobility spectrometer ("IMS") having a generally tubular housing 1 with an analysis or drift region 2 towards its right-hand end (as shown in FIG. 1) and an ionization of reaction region 3 towards its opposite left-hand end (as shown in FIG. 1).

An inlet conduit 4 opens at one end 5 to air or another source of gas or vapor to be sampled and analyzed. Air or gas is drawn through the inlet conduit 4 by means of a pump 6 connected at the opposite end of the inlet conduit 4. At some point along the inlet conduit 4, an inlet passage 7 which may be provided by a capillary passage or a pin-hole communicates between the inlet conduit 4 and the interior of the reaction region 3 so that molecules of interest can pass along a gas flow path from the inlet conduit 4 into the reaction region 3. The inlet conduit 4 of the apparatus includes a preconcentrator 9. The preconcentrator 9 may be provided as a coating of adsorbent material on the inlet passage 7 itself, or as a separate preconcentrator 9' apparatus that is mounted in the inlet conduit 4 adjacent the inlet passage 7. A pressure pulser 8, which may be an electromagnetic transducer similar to a loudspeaker, is connected to the housing 1 in the manner described in U.S. Pat. No. 6,073,498, to Taylor et al., which is hereby incorporated herein by reference. The pressure pulser 8 is operated in a manner described in detail below.

The reaction region 3 contains apparatus to ionize molecules of the analyte substance, such as a corona discharge point 10, at a high potential. The reaction region 3 and the drift region 2 are both at atmospheric pressure or just slightly below atmospheric pressure. The reaction region 3 and the drift region 2 may be separated from one another by an optional, conventional electrostatic shutter 11 such as a Bradbury Nielson gate by which the flow of ions into the drift region 1 may be controlled. The drift region 2 has a series of pairs of electrodes 12 on opposite sides thereof which are longitudinally spaced from one another along the length of the drift region 2. A voltage supply 13 applies a voltage to each electrode pair 12, which voltage increases from the left to the right along the length of the drift region 2 (as shown in FIG. 1) so that ions passed by the electrostatic shutter 11 are subject to a voltage gradient, which draws them along the length of the drift region 2. A collector plate 14 mounted at the far, right-hand end of the drift region 2 (as shown in FIG. 1) collects ions after passage along the drift region 2. The charge produced by each ion when it impacts the collector plate 14 is supplied as an electrical signal to a processor unit 15. The processor unit 15 analyzes the signals to produce spectra representative of the mobility of the different ions detected and supplies these to a display or other utilization apparatus 16.

As in conventional IMS apparatus, a gas flow system 20 provides a flow of clean dry air along the inside of the housing 1 against the flow of the ions. The gas flow system 20 includes a pump 21 with molecular sieve inlet and outlet filters 22 and 23 respectively located at its inlet and outlet. The inlet filter 22 connects with an inlet pipe 24, which opens into the housing 1 towards the inlet end of the reaction region 3 (shown on the left end in FIG. 1). The outlet filter 23 connects with an outlet pipe 25, which opens into the housing 1 towards the downstream end of the drift region 2 (shown on the right end in FIG. 1). The pump 21 operates to draw gas from the reaction region 3 so that it flows through the first filter 22, the pump 21 and the second filter 23 before flowing back into the housing 1 at the right-most end of the drift region 2 (as shown in FIG. 1).

The apparatus is switched between two alternating phases, namely an adsorb phase during which the preconcentrator 9 or 9' adsorbs analyte substance contained in gas supplied at the one end 5 of the inlet conduit 4, and a desorb phase during which the preconcentrator desorbs the adsorbed substance and releases it for supply to the interior of the apparatus for ionization and detection. During the first, adsorb phase shown in FIG. 1, the pressure pulser 8 is energized by the processor 15 to produce short, regular, alternating negative and positive pressure pulses (as illustrated) inside the housing 1. This causes air in the conduit 4 to "pant" in and out of the inlet passage 7 and, in so doing, it flows backwards and forwards in an alternating fashion over the surface of the preconcentrator 9 or 9'. Analyte substance in the air is, therefore, adsorbed into the preconcentrator 9 or 9' as it is drawn in towards the interior of the housing 1, and the air returned in the opposite direction will have a much depleted concentration of the analyte substance. The "panting," alternating flow ensures that there is no net flow in either direction, and the phase, amplitude, and frequency of the "panting" is selected such that sample vapor is not jetted far enough into the reaction region 3 to be ionized and detected. The processor 15 maintains this adsorb phase for sufficient time to ensure that a detectable amount of sample vapor is adsorbed onto the preconcentrator 9 or 9'. Typically, this would be for anywhere from a few seconds to a few tens of seconds.

Figure 2:
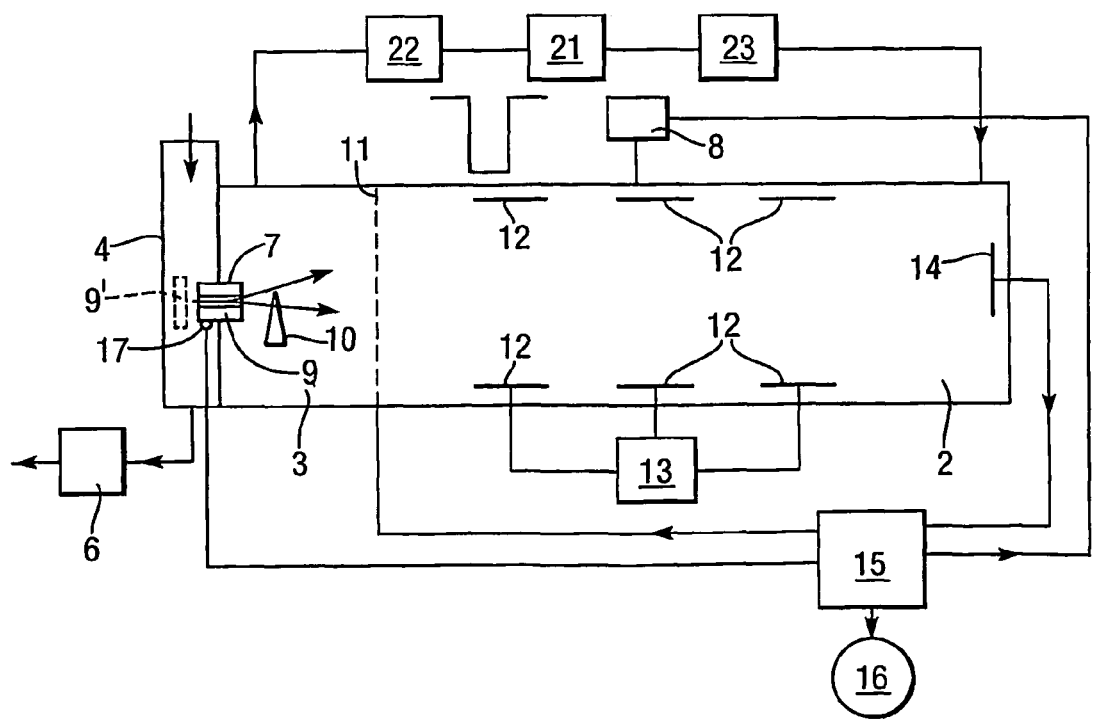
FIG. 2 shows the apparatus schematically during a desorb phase.

The processor 15 then switches to the desorb phase shown in FIG. 2. First, the processor 15 stops the pressure pulser 8 from making regular alternating pressure cycles. Then, the processor 15 energizes a heater 17 that is mounted on the preconcentrator 9 or 9' to raise its temperature and cause thermal desorption of the analyte sample vapor. There are other ways in which a preconcentrator can be caused to release the adsorbed substance, such as by subjecting it to radiation, pressure, vibration, or the like. The desorbed analyte sample vapor is then transferred into the reaction region 3 by causing flow through the inlet passage 7 and beyond into the reaction region 3. This flow could be continuous and could be achieved by a separate pump (not shown). Alternatively, it could be caused by a larger, momentary pressure reduction or negative pulse (as illustrated) in the housing 1 induced by the pressure pulser 8. This jets the desorbed vapor into the reaction region 3 sufficiently to enable ionization and detection. This could be combined with a "sipping" process in which the pressure pulser 8 is energized to draw repeated small amounts into the reaction region.

The present invention can be used to enable small concentrations of analyte to be detected with an improved signal-to-noise ratio. The invention is particularly useful in IMS apparatus, but may also have application in other forms of detector. The invention may also be useful in applications other than detection where it is necessary to increase the concentration of a substance.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A detector apparatus comprising:
   an inlet; and
   a preconcentrator located adjacent the inlet, wherein the detector apparatus is arranged and configured to cause an alternating flow of analyte gas or vapor across the preconcentrator during an adsorb phase such that there is a low or no net flow of gas or vapor into the detector apparatus and such that an analyte substance of interest is adsorbed by the preconcentrator; and
   wherein the detector apparatus is arranged and configured to cause the preconcentrator to desorb during a desorb phase and to interrupt the alternating flow and produce a net flow of gas or vapor into the detector apparatus such that the desorbed analyte substance is carried into the detector apparatus.

2. The detector apparatus defined in claim 1, wherein the detector apparatus additionally comprises:
   a pressure pulser connected with the interior of the detector apparatus which effects the alternating flow.

3. The detector apparatus defined in claim 1, wherein the detector apparatus additionally comprises:
   a thermal device which causes the preconcentrator to desorb.

4. The detector apparatus defined in claim 1, wherein the detector apparatus comprises an ion mobility spectrometer apparatus, and wherein the analyte gas or vapor is admitted during the desorb phase sufficiently to be ionized in a reaction region of the detector apparatus.

5. The detector apparatus defined in claim 1, wherein the preconcentrator is located in a passage opening into the interior of the detector apparatus.

6. A method of increasing the concentration of a substance comprising the steps of:
   providing a preconcentrator that is arranged and configured to adsorb and desorb the substance;
   providing, during an adsorption phase, an alternating flow of gas or vapor in a passage and over the preconcentrator so that the substance is adsorbed by the preconcentrator and there is substantially no net flow of gas or vapor along the passage; and
   subsequently, during a desorption phase, causing the preconcentrator to desorb the adsorbed substance and provide a net flow of gas or vapor along the passage so that the desorbed substance is carried with the gas or vapor along the passage.

7. A preconcentrator apparatus that is arranged and configured to adsorb and desorb a substance, the preconcentrator apparatus comprising:
   a gas flow path; and
   an adsorbent material in the gas flow path;
   wherein the preconcentrator apparatus is operable in conjunction with an apparatus that effects during an adsorption phase an alternating flow of gas or vapor over the preconcentrator apparatus and in the gas flow path whereby the substance is adsorbed by the preconcentrator apparatus and there is substantially no net flow of gas or vapor along the gas flow path;
   wherein the preconcentrator apparatus is arranged and configured to cause the preconcentrator apparatus to desorb the adsorbed substance during a subsequent desorption phase; and
   wherein the preconcentrator apparatus is arranged and configured to provide a net flow of gas or vapor along the gas flow path during the desorption phase so that the desorbed substance is carried with the gas or vapor along the gas flow path.

8. The preconcentrator apparatus defined in claim 7, the apparatus that effects the alternating flow of gas or vapor comprises a pressure pulser.

9. A detector apparatus comprising:
   a housing having a first end at which an analyte gas or vapor will be admitted to the housing and a second end opposite the first end;
   a reaction region located in the housing adjacent the first end thereof;
   a drift region located in the housing between the reaction region and the second end of the housing;
   an inlet via which an analyte sample may be admitted into the reaction region;
   a preconcentrator located outside the housing adjacent the inlet;
   an alternating flow driving apparatus that selectively causes an alternating flow of analyte gas or vapor across the preconcentrator during an adsorb phase such that there is a low or no net flow of gas or vapor into the reaction region and such that an analyte substance of interest is adsorbed by the preconcentrator; and
   a net flow driving apparatus that selectively interrupts the alternating flow and produce a net flow of gas or vapor into the detector apparatus, causes the preconcentrator to desorb during a desorb phase, and carries a desorbed analyte substance into the reaction region.

10. The detector apparatus defined in claim 9, wherein the alternating flow driving apparatus comprises:
    a pressure pulser connected with the interior of the detector apparatus which effects the alternating flow.

11. The detector apparatus defined in claim 10, wherein the pressure pulser produces short, regular, alternating negative and positive pressure pulses inside the housing to causes analyte gas or vapor to "pant" in and out of the inlet and, in so doing, to flows backwards and forwards in an alternating fashion over the preconcentrator.

12. The detector apparatus defined in claim 9 wherein the net flow driving apparatus comprises:
    a pressure pulser connected with the interior of the detector apparatus which effects the net flow.

13. The detector apparatus defined in claim 12, wherein the pressure pulser produces a larger, momentary pressure reduction or negative pulse in the housing to jet the desorbed analyte substance into the reaction region.

14. The detector apparatus defined in claim 9, additionally comprising:
    a thermal heater which selectively causes the preconcentrator to desorb during the desorb phase.

15. The detector apparatus defined in claim 9, additionally comprising:
    an inlet conduit having a first end to which an analyte substance of interest may be supplied and a second end, the inlet being in fluid communication with the inlet conduit, the preconcentrator being located in the inlet conduit.

16. The detector apparatus defined in claim 9, wherein the preconcentrator is located within the inlet.

17. The detector apparatus defined in claim 16, wherein the preconcentrator comprises:
    a coating on an inner surface of the inlet.

18. The detector apparatus defined in claim 9, additionally comprising:
    an ionizing apparatus located in the reaction region that ionizes molecules of the analyte gas or vapor that has been admitted to the reaction region.

19. The detector apparatus defined in claim 9, additionally comprising:
an electrostatic shutter that controls the flow of ions from the reaction region to the drift region.

20. The detector apparatus defined in claim 9, additionally comprising:
a plurality of longitudinally spaced-apart electrode pairs located in the drift region that establish an electrical field in the drift region which draws ions located in the drift region in a direction from the first end of the housing to the second end of the housing.

21. The detector apparatus defined in claim 9, additionally comprising:
a collector plate located near the second end of the housing, the collector plate collecting ions passing to the second end of the housing and providing an output to a processor indicative of the ions detected by the collector plate.

* * * * *